United States Patent [19]

Weinzerl et al.

[11] Patent Number: 5,357,798
[45] Date of Patent: Oct. 25, 1994

[54] PROCESS FOR DETERMINING A SAFETY MARGIN FOR A TRAVELING MOTOR VEHICLE

[75] Inventors: Alfred Weinzerl; Jürgen Holzinger, both of Graz; Wolfgang Hirschberg, Ulrich/Steyr, all of Austria

[73] Assignee: Steyr-Daimler-Puch AG, Wien, Austria

[21] Appl. No.: 6,841

[22] Filed: Jan. 21, 1993

[51] Int. Cl.$^5$ ............... E01C 23/00; G01M 17/02
[52] U.S. Cl. ............... 73/146; 364/426.02; 73/9
[58] Field of Search ............... 73/146, 178 R, 8, 9; 364/426.02, 443; 303/100, 102, 97, 103

[56] References Cited

U.S. PATENT DOCUMENTS

| | | | |
|---|---|---|---|
| 3,772,698 | 11/1973 | Furia | 73/146 |
| 3,948,080 | 4/1976 | Boyd | 73/9 |
| 4,902,076 | 2/1990 | Ushijima et al. | 364/426.02 |
| 4,974,163 | 11/1990 | Yasuno et al. | 364/426.02 |
| 4,980,831 | 12/1990 | Katayama et al. | 364/426.02 |
| 5,079,709 | 1/1992 | Hirako et al. | 364/426.02 |
| 5,117,934 | 6/1992 | Tsuyama et al. | 364/426.02 |
| 5,119,299 | 6/1992 | Tamura et al. | 364/426.02 |
| 5,124,922 | 6/1992 | Akiyama | 364/426.02 |

FOREIGN PATENT DOCUMENTS

| | | |
|---|---|---|
| 3644139 | 7/1988 | Fed. Rep. of Germany . |
| 3735673 | 5/1989 | Fed. Rep. of Germany . |
| 4010507 | 10/1991 | Fed. Rep. of Germany . |

*Primary Examiner*—Richard E. Chilcot, Jr.
*Assistant Examiner*—William L. Oen
*Attorney, Agent, or Firm*—Meltzer, Lippe, Goldstein, et al.

[57] ABSTRACT

A process for determining a safety margin with respect to adhesion between tires and roadway of a travelling motor vehicle comprises, detecting longitudinal and transverse acceleration values (ax, ay), a rotational wheel acceleration value (Phi), and a dynamic steering angle value, and producing signals indicative thereof. A longitudinal adhesion value (Six) is determined as a function of the longitudinal acceleration (ax) and the rotational wheel acceleration (Phi), while a transverse adhesion value (Siy) is determined as a function of the transverse acceleration (ay) and the dynamic steering angle. Maximum attainable longitudinal and transverse acceleration values (axLIM, ayLIM) are next determined by multiplying the longitudinal and transverse acceleration values (Six, Siy) by vehicle specific coefficients (Kx, Ky) and a limit curve (aLIM), e.g., an ellipse, is established. Next a current vehicle movement state vector (AF) is formed by a vectorial combination of the longitudinal and transverse acceleration values (ax, ay). A safety margin value (SAFLIM) is obtained by comparing the lengths of the vehicle movement state vector (AF) with a collinear limit vector (AMAX) which reaches the limit curve (aLIM), and the safety margin value (SAFLIM) is displayed to the driver. Desirably, if the safety margin value (SAFLIM) exceeds predetermined threshold values, perceptible warning signals, e.g., a yellow light and then a red light, are triggered.

10 Claims, 9 Drawing Sheets

$$DE\_ACK = \arctan \frac{WB}{RADIUS}$$

$$RADIUS = \frac{RVS^2}{ay}$$

$$DEK = AST - DE\_ACK$$

PROCESS FOR DETERMINING A SAFETY MARGIN FOR A TRAVELING MOTOR VEHICLE

BACKGROUND OF THE INVENTION

The instant invention relates to a process for determining a safety margin with respect to adhesion between the tires and the roadway for motor vehicles during the dynamics of vehicle movement.

Even with all the progress achieved until now in safety technology for motor vehicles, the sudden deterioration of adhesion between tires and roadway which surprises the driver, or is not noticed in sufficient time, still represents a great safety gap. The danger of misjudgments or surprise exists not only when braking, but primarily when entering into curves where even a minor decrease of frictional adhesion to the roadway can have serious consequences.

This danger is even greater with all-wheel drive vehicles which give the driver a subjective feeling of safety. Furthermore, the transition between safety and danger zones is relatively narrower for such vehicles than for conventional vehicles.

Continued progress in safety technology therefore requires that the driver be given a qualified warning as early as possible when the adhesion begins to decrease to a dangerous level. In this case, "qualified" means above all that the warning should reveal how far away the vehicle still is from a danger level.

A process for determining this safety margin is known from DE-C 40 10 507. In this patent document, a characteristic curve is derived and stored from value pairs of the wheel slip and a simultaneously acting peripheral force during stationary or quasi-stationary operating states on a dry roadway while assuming a constant value for the coefficient of friction $\mu$. If later value pairs occur which are not located on this characteristic curve, the conclusion is drawn that adhesion has deteriorated and that a different value for the coefficient of friction $\mu$ applies, i.e., one which represents a rise in the slope of the curve determined by the new value pair.

To speak of a coefficient of friction value $\mu$ between tires and roadway in connection with load transmission is generally controversial because it is not constant and because this is a very complex process which has little to do with the friction between rigid bodies described by Coulomb's theory. Although only the approximately linear micro-area of the slip curve is used in this known process, there still remains the question how an adhesion value can be determined in the limit zone of the slip curve which is in no case linear.

Furthermore, it may be viewed as disadvantages of this known process that a measurement of the peripheral force on the wheel is required, necessitating intervention into the drive train, and that a wheel slip signal (indicating the difference between the rotational speeds of the driven and non-driven wheels) is required, so that the process cannot be used for all-wheel drive vehicles, for instance. The advantage of continuous detection, even in unchanging travel, must also be weighed against the fact that this evaluation of an adhesion value only takes into account the peripheral elasticity of the tire (i.e., takes into account only tire slip during acceleration or deceleration), without taking into account the transverse elasticity of the tires which is lower and is therefore easier to measure and more indicative than peripheral elasticity.

The situation is similar with the process known from DE-A 37 35 673 where the circumferential acceleration of the driven wheels is measured by using a differential method and is converted by computation into a frictional value $\mu$ while taking into account constructive magnitudes of the drive train.

Finally, DE-A 36 44 139 teaches a process which compares the acceleration calculated from the rotational wheel speeds with a longitudinal acceleration measured by an acceleration sensor attached to the vehicle. However, this is done only for a plausibility control of the input signals for ABS or ASR systems.

It is therefore the object of the instant invention to propose a process making it possible to detect the safety margin for a vehicle's adhesion to the roadway while taking into account all driving conditions and actually attainable limit zones, which process requires no intervention into the drive train, and which is equally suited for conventional vehicles and all-wheel drive vehicles.

SUMMARY OF THE INVENTION

In accordance with the present invention, a process for determining a safety margin with respect to adhesion between tires and roadway of a travelling motor vehicle comprises, detecting longitudinal and transverse acceleration values (ax, ay), a rotational wheel acceleration value ($\ddot{\Phi}$i), and a dynamic steering angle value for the vehicle, and producing signals indicative thereof. From these signals, a longitudinal adhesion value (Six) is determined as a function of the longitudinal acceleration (ax) and the rotational wheel acceleration ($\ddot{\Phi}$i), while a transverse adhesion value (Siy) is determined as a function of the transverse acceleration (ay) and the dynamic steering angle. Maximum attainable longitudinal and transverse acceleration values (axLIM, ayLIM) are next determined by multiplying the longitudinal and transverse acceleration values (Six, Siy) by vehicle specific coefficients (Kx, Ky) and a limit curve (aLIM), e.g., an ellipse, is established. Next, a current vehicle movement state vector (AF) is formed by a vectorial combination of the longitudinal and transverse acceleration values (ax, ay). A safety margin value (SAFLIM) is then obtained by comparing the lengths of the vehicle movement state vector (AF) with a collinear limit vector (AMAX) which reaches the limit curve (aLIM), and an indication of the safety margin value (SAFLIM) is displayed to the driver. Desirably, if the safety margin value (SAFLIM) exceeds predetermined threshold values, perceptible warning signals, e.g., a yellow light and then a red light, are triggered.

More particularly, in accordance with the present invention, adhesion values in both the longitudinal and transverse directions, which are considerably different from each other (as the longitudinal elasticity becomes progressively very different from the transverse elasticity), are determined separately so that not only braking and acceleration, but also turning and even combined driving states (e.g., braking in a curve) are covered. The latter is especially important for driving safety because the individual adhesion values are lower in combined driving states, as was traditionally illustrated by the so-called "friction circle."

It is an advantage of the present invention that only vehicle movement values are used which are easily determined even for all-wheel drives. Therefore, only an acceleration sensor for longitudinal and transverse directions and possibly also a steering angle sensor need to be installed in a vehicle already equipped with an ABS or ASR system.

It is a further advantage of the inventive process that the adhesion values are defined as proportional to the longitudinal and transverse acceleration and increase up to the maximum attainable accelerations. The adhesion values themselves, however, are not linear functions of the vehicle movement values from which they are derived, but exclude the assumption of a constant coefficient of frictional value $\mu$. Because of the definitions, the maximum attainable accelerations can be determined by multiplying the momentary adhesion values with vehicle-specific coefficients representing limit values actually attained in driving tests.

In the process according to the instant invention, the adhesion values are determined by:
evaluating the steering angle requirement for existing transverse acceleration, then
evaluating the rotational wheel speed requirement for a given travel speed, and finally
forming a vectorial combination of these two results.

From the separately determined maximum attainable longitudinal and transverse accelerations and through the vectorial combination, a complete limit curve, which is applicable even to mixed driving states (e.g., braking in a curve), can be drawn in the manner of the previously mentioned "friction circle."

The assumption of the proportional evolution of the adhesion values and their separate determination also make it possible to combine the momentary measured longitudinal and transverse accelerations into a vector and to determine the actually still-available safety margin by comparison with the limit curve. Qualified warning when the vehicle approaches the danger zone thus becomes possible.

If as recent as possible a limit curve is to be available at all times, even during very long straight travel without acceleration or deceleration, such a curve is stored and is always corrected when a change in longitudinal or transverse acceleration occurs in a state of vehicle movement. In this case, the representation of maximum attainable longitudinal and transverse acceleration in the form of a closed limit curve has the great advantage that only one single value pair (whether one of the two values is zero or not) suffices in order to enlarge the limit curve or to reduce it. This would be inapplicable only if the roadway were textured differently in different directions.

Although very different possibilities exist for defining the adhesion values from the four mentioned vehicle movement state values, it has been shown that especially great precision can be achieved if they are calculated from analytically represented functions, whereby the coefficients of the analytical representations are obtained from values determined in tests or simulation.

This manner of proceeding ensures an excellent approximation of the actual conditions. Although the determination of the values by test or simulation appears to be costly, such tests are usually carried out anyway for other purposes during the development of a vehicle. Thus, the particularities of the friction value which make it impossible to treat it conventionally become part of these values and can be fully taken into account by appropriate additions for the analytical representation of the functions.

In order to give the driver a meaningful indication of the safety margin determined in accordance with the invention, and in order to save him from having to read yet another display on the dashboard, it has been shown to be sufficient and even especially effective to first compare the safety margin with defined threshold values and to trigger warning signals when these are exceeded. In this case, the threshold values can be appropriately staggered and the warning signals can vary in loudness, brightness or form.

In order to avoid false alarms which would inure the driver against warnings, it is advantageous to establish limits for the adhesion values or values of the safety margin outside of which they are no longer taken into account.

In a refinement of the process according to the invention, it is furthermore advantageous to introduce the steering angle signal delayed by a delay-time element into the calculation of the adhesion values. The sluggishness of the reaction of the tire running surfaces to the steering wheel movements, which can be considerable with belted tires, is thus taken into account. Without the delay-time element it may occur that a great transverse slip is ascertained inappropriately with small but rapid steering wheel movements, resulting in a false alarm.

Finally, it is also possible within the framework of the invention to make a correction while taking into account the slope of the roadway when determining the adhesion values. In this manner, even strongly convex road surfaces which would cause a steering swing without corresponding transverse acceleration (possibly resulting in a false alarm) are also taken into account.

BRIEF DESCRIPTION OF THE DRAWINGS

The process according to the invention is explained in greater detail below through the drawings, in which.

DETAILED DESCRIPTION OF A PREFERRED EMBODIMENT

Figure 1:
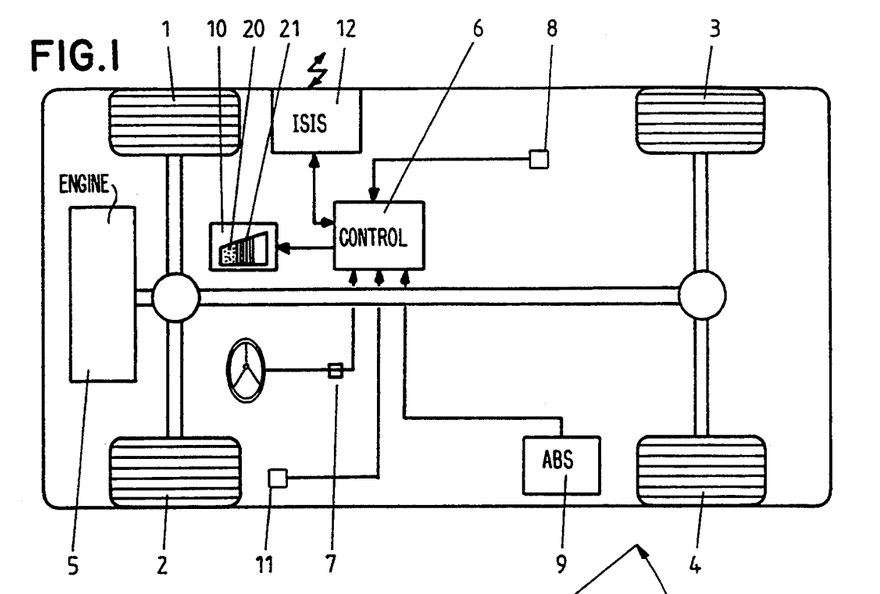
FIG. 1 is a schematic representation of a vehicle suitable for the application of the process according to the invention.

A vehicle suitable and equipped for the application of the process according to the invention, in this case an all-wheel-drive vehicle, is shown schematically in FIG. 1. The front wheels 1, 2 and/or the rear wheels 3, 4 are driven by an engine 5 in any desired and known manner.

The process according to the invention is carried out by a control device 6 which is supplied by a steering angle sensor 7, at least one acceleration sensor 8, and an ABS device 9 with the following input signals: steering angle AST, longitudinal and transverse accelerations ax and ay, and rotational wheel speeds n1, n2, n3, n4. The output signal of the control device 6 is transmitted to a display 10 which may, for example, consist of a sequence of yellow and red warning lights 20, 21 and is preferably installed on the dashboard of the vehicle. Alternatively, the output signal from control device 6 may be displayed in some other form, for example, by means of a meter. In addition, a connection is provided to a diagnostics interface 11 which is accessible from the outside and to an ISIS unit 12 which allows for wireless data exchange with fixed installations.

Figure 2:
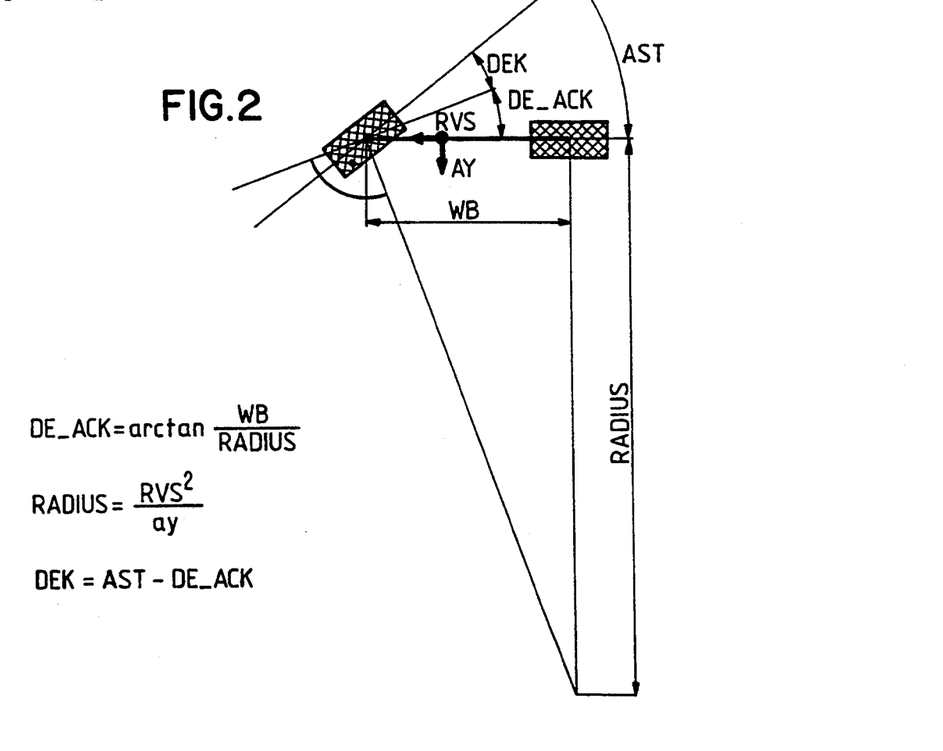
FIG. 2 is a schematic representation of a motor vehicle traveling through a curve.

The computations of the process according to the invention are carried out as follows:

A corrected steering angle DEK is derived from the measured steering angle AST according to the relationships shown in FIG. 2. For this purpose, the measured steering angle AST is reduced by a kinematic component DE_ACK which is calculated from the arctangent of the length of the wheel base WB divided by the curve radius. In this case, the curve radius is calculated as the square of the longitudinal velocity RVS of the vehicle divided by the build-up acceleration ay. The latter values can be determined from the rear wheel rpm's, for example.

Figure 3:
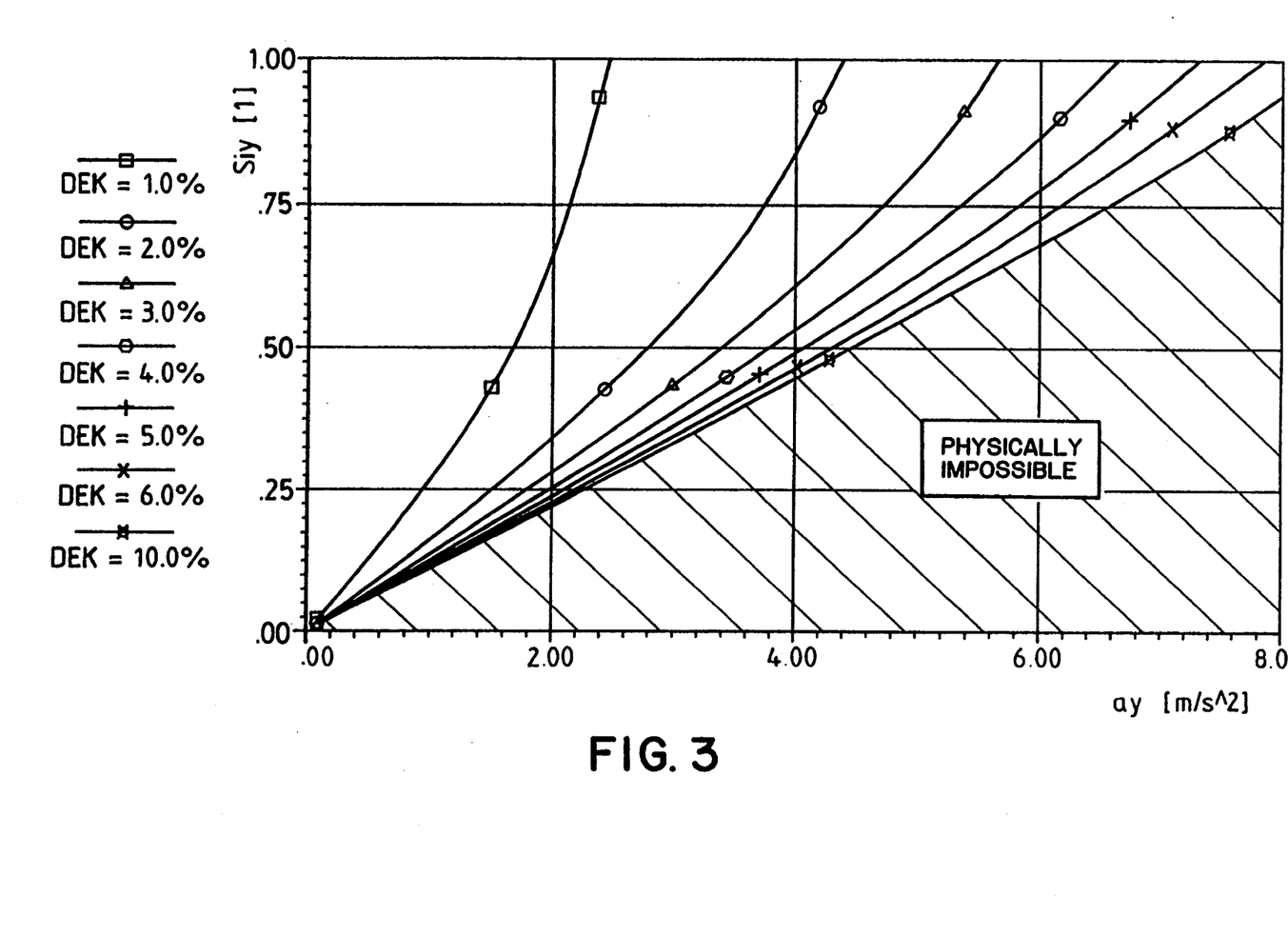
FIG. 3 shows a diagram of adhesion values in the transverse direction (Siy) as a function of transverse acceleration (ay) for different steering angles (DEK)

The adhesion value in the transverse direction Siy is now defined as a function of the corrected steering angle DEK and of the transverse acceleration ay. This function corresponds to a surface in a three-dimensional system of coordinates which is shown in FIG. 3 by sections for different corrected steering angles DEK. In this drawing, ay is shown along the x-axis and Siy along the y-axis. This surface may be described analytically as a polynomial formulation, the coefficients of which are calculated from vehicle-specific measurements or simulation calculations and which are stored in the memory of the control device 6 for later determination of the adhesion value Siy from measured value pairs of ay and DEK.

The polynomial formulation may look as follows:

$$Siy = A(DEK)ay + B(DEK)ay^3 + C(DEK)ay^5$$

where $$A(DEK) = A0 + \frac{A1}{DEK} + \frac{A2}{DEK^2}$$

$$B(DEK) = B0 + \frac{B1}{DEK} + \frac{B2}{DEK^2}$$

$$C(DEK) = C0 + \frac{C1}{DEK} + \frac{C2}{DEK^2}$$

The adhesion value in the longitudinal direction Six of the vehicle is calculated from the rotational wheel speeds n1, n2, n3 and n4, obtained from the ABS system 9, and the longitudinal acceleration ax. Direct measurement of the wheel slip is not necessary but may be calculated from the longitudinal acceleration ax and the rotational wheel speed of a driven wheel. If the relationship $$\text{Slip } Sl = \frac{V_x - r_e \ddot{Phi}}{V_x}$$

wherein $V_x$ is the longitudinal speed of the car and $r_c$ is the effective wheel radius, is differentiated and transformed, the result is that the rotational wheel acceleration $\ddot{Phi}$ is the product of the longitudinal build-up acceleration ay and a magnitude determined by the adhesion conditions, divided by the actual tire radius. In this case, $r_c$ depends on the load on the wheel which in turn depends on the longitudinal acceleration taking into account longitudinal dynamics. This justifies regarding the adhesion value in the longitudinal direction Six as a function of the longitudinal acceleration ax and of the rotational wheel acceleration $\ddot{Phi}$. By means of simulation calculations based on this relationship it has been ascertained that the front wheels are better suited for evaluating adhesion.

Figure 4:
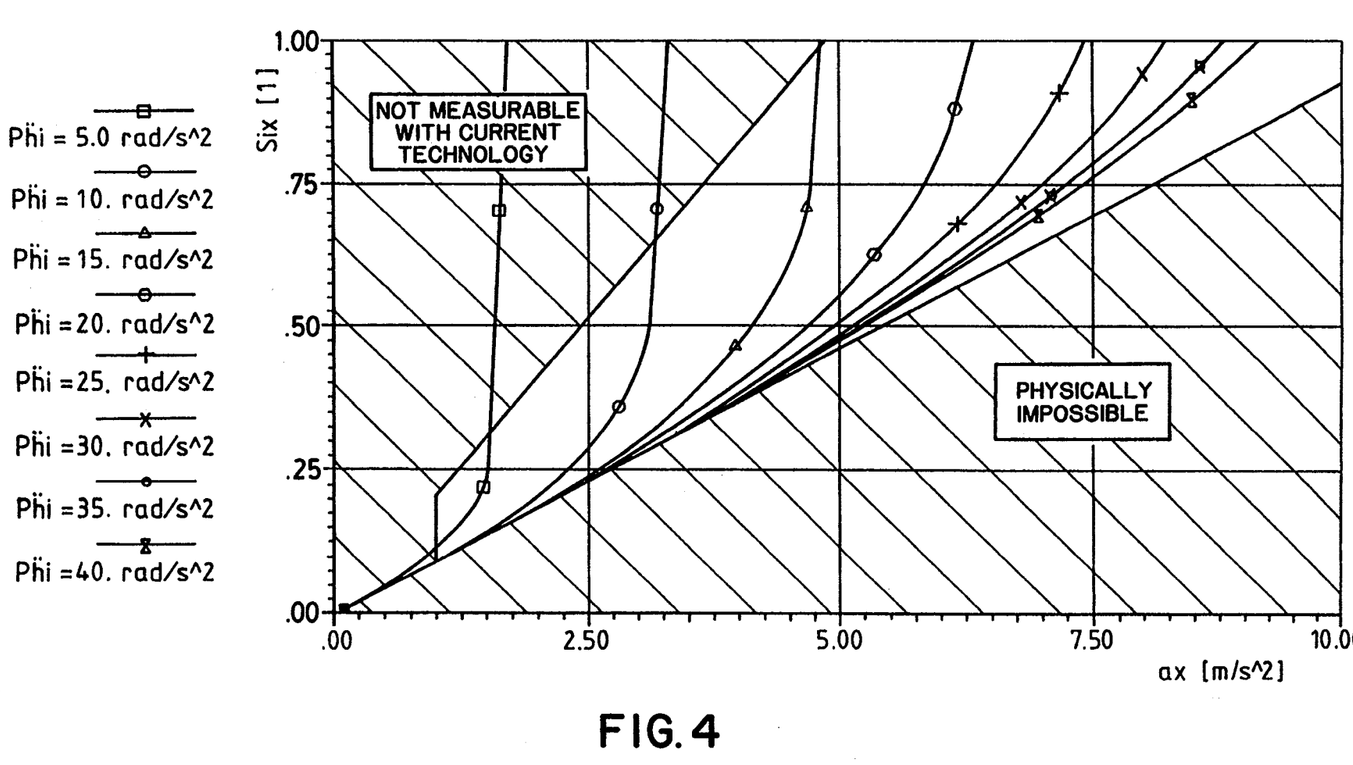
FIG. 4 shows a diagram of adhesion values in the longitudinal direction (Six) as a function of longitudinal acceleration (ax) for different rotational wheel accelerations (Phi)

The function for the adhesion value in longitudinal direction Six may also be represented by a surface in a three-dimensional system of coordinates (strictly speaking two surfaces, one for positive and one for negative acceleration) which is also shown as a group of two-dimensional curves in FIG. 4 by sections along planes of constant angular acceleration. The longitudinal acceleration ax is shown along the x-axis, while the adhesion value in the longitudinal direction Six is shown along the y-axis for different values of rotational wheel acceleration $\ddot{Phi}$. It can be seen that the curves are very steep at lower wheel accelerations, making an analytical representation of this surface more difficult. A suitable formulation, using the methods described in the SAE paper 870421(1987) could look as follows:

$$Six = \frac{1}{B(\ddot{Phi})} \tan\left(\frac{1}{C(\ddot{Phi})} \arcsin \frac{ax}{D(\ddot{Phi})}\right)$$

where
$B(\ddot{Phi}) = B2 \sin(B1 \arctan(B0\ \ddot{Phi}))$
$C(\ddot{Phi}) = C0 + C1\ \ddot{Phi} + C2\ \ddot{Phi}^2$
$D(\ddot{Phi}) = D0 + D1\ \ddot{Phi} + D2\ \ddot{Phi}^2$ Here again the individual coefficients for the analytical representation of the surface are calculated from test and/or simulation results and the function Six is stored in the memory of the control device 6 for later utilization.

Because of measuring errors, especially when measuring the longitudinal acceleration, and because of the background interference with measurement, the hatched zone shown at the top of FIG. 4 is not accessible by current measuring techniques and values in this zone have therefore been eliminated. The lower hatched zone is physically not possible. This means that during acceleration or braking a useable signal is produced only after utilization of approximately 50% of the maximum attainable longitudinal acceleration.

When the vehicle is traveling, measured values of ay, DEK, ax, and Phi are supplied continuously to the control device 6 and the adhesion values Six, Siy are calculated from the latter in real time and subsequently from this the maximum attainable accelerations axLIM, ayLIM are calculated by multiplying Six and Siy with the vehicle specific coefficients Kx, Ky. The latter coefficients describe the actual limit zone of the vehicle determined by tests and are stored in the memory of the control device 6. This methodology is justified by the assumption of the adhesion values as being proportional and by the quality of the stored functions.

Figure 5:
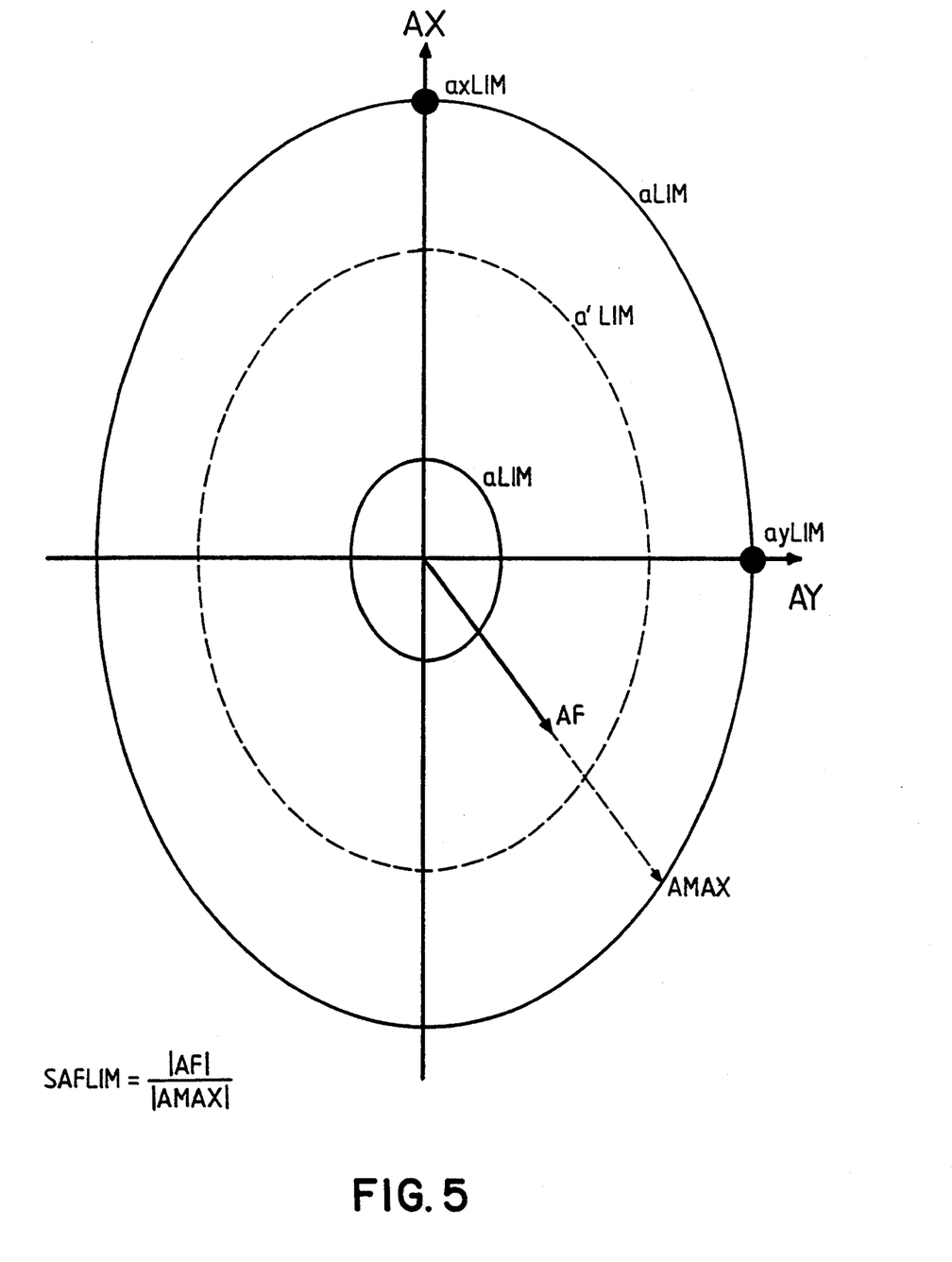
FIG. 5 is a schematic representation of a limit curve derived from maximum accelerations and vehicle movement vectors.

The maximum attainable accelerations values axLIM, ayLIM are shown in FIG. 5 on the axes of the system of coordinates and from this the limit curve aLIM is produced by drawing in "quarter ellipses." For this purpose, it is advantageous to distinguish between an axLIM value for acceleration and an axLIM value for braking. During operation this (and the subsequent events) occur in computational real time, and the applicable limit curve at any moment is also stored in the memory of the control device 6. The outer curve aLIM in FIG. 5 represents the limit curve for conditions of high adhesion, e.g., on a dry, gripping road, and the inner limit curve aLIM represents conditions of low adhesion, for example, on a roadway covered with snow. When the adhesion values Six and/or Siy which are constantly being calculated change during travel, an updated limit curve a'LIM is calculated through affine transformation (shown by a dashed line) and replaces the stored one.

In the right lower quarter of the ellipse shown in FIG. 5, the current vehicle movement state is represented by vector AF with its components ax and ay, and the collinear limit vector AMAX reaching the present limit curve aLIM together with its components axMAX and ayMAX are shown. The used-up distance to the limit zone SAFLIM is obtained by dividing the absolute values of these two vectors as indicated on FIG. 5. When the outer limit curve aLIM shrinks down to the size of limit curve a'LIM which is represented by a dashed line because of a change in road conditions, and the limit vector AMAX is reduced while the present vehicle movement state vector AF remains unchanged, the quotient of their absolute values and SAFLIM, the used-up distance to the limit zone, increase.

When SAFLIM rises above a predetermined limit value, a yellow warning light 20 lights up on the display device 10. When a second predetermined limit value of SAFLIM is exceeded, the red warning light 21 also lights up.

The sequence of steps in a program for carrying out the inventive process is now described by reference to FIGS. 6A–6D. This program runs cyclically in the microcomputer of the control device 6.

The specific data characterizing the current stage of vehicle movement supplied by the steering angle sensor 7, the acceleration sensor 8, and the ABS device 9 are edited at 40 (FIG. 6A) and are available for the subsequent steps. Data editing comprises filtering, A/D conversion, correction, calibration, filtering and differentiation to produce differentiated signals. The processing of the steering angle signal will be explained further below with reference to FIG. 7.

At 41 the longitudinal speed RVS is compared with a minimum value RVSLIM. As long as RVSLIM has not yet reached this value (approx. 10 km/h), the program is directed by connecting line 70 to box 54 (FIG. 6B) where no adhesion value can be determined, and the program then goes to the final box 50 (FIG. 6A) where the cycle starts again.

If the longitudinal build-up speed RVS exceeds RVSLIM, the decision is made at 42 whether the derivative of the vertical acceleration AZDIF is greater than a predetermined limit value AZDIFLIM. If yes, no new computation of the adhesion value is carried out and the old value is preserved at 49. If not, the decision is made at 43 whether the steering angle AST is greater than a limit value ASTLIM. If not, no determination of adhesion in transverse direction can be made and the connecting line 71 directs the program to box 55 (FIG. 6B) to be discussed further below.

Figure 6A:
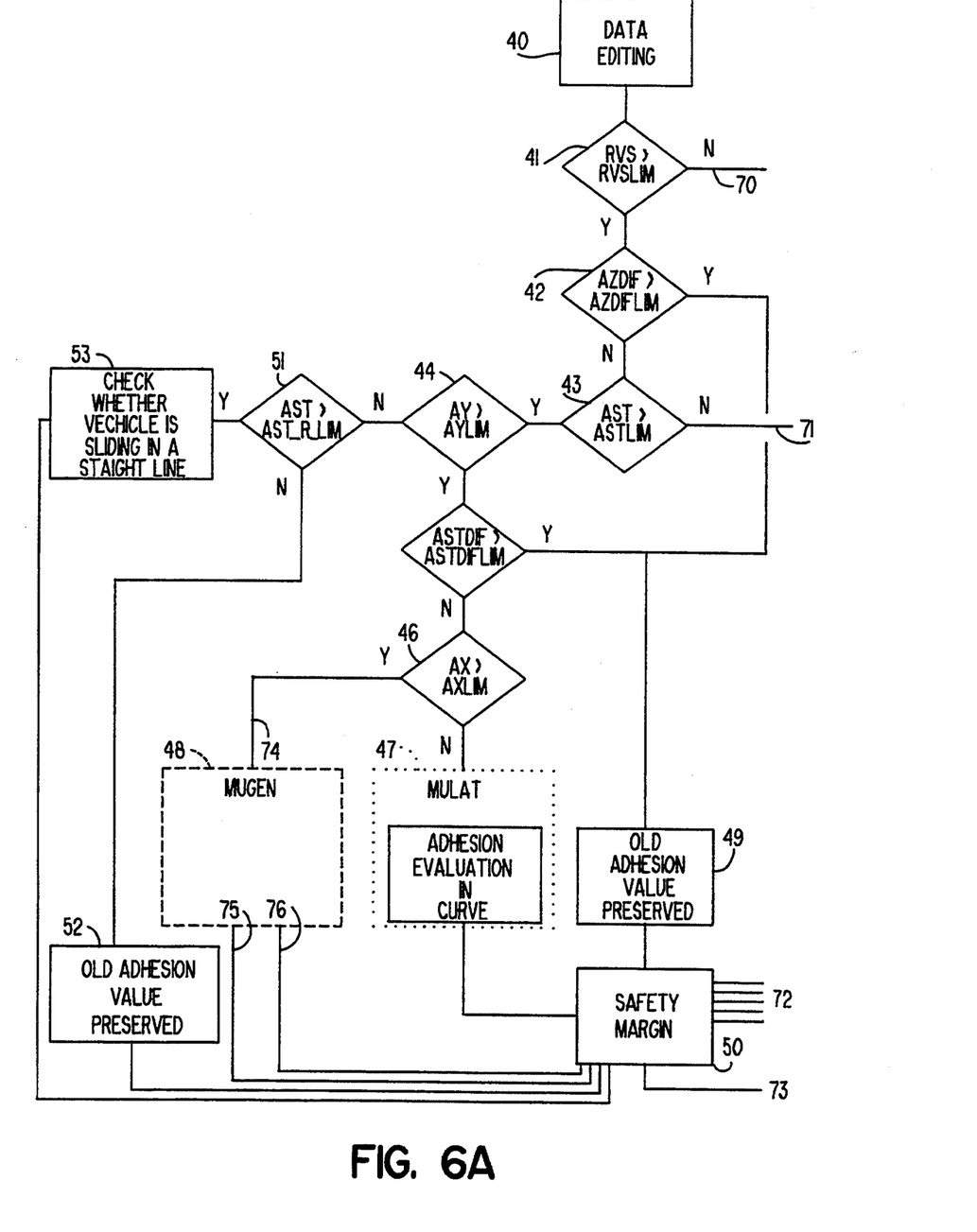
FIGS. 6A–6D show a flowchart of a program for carrying out the inventive process.
Figure 6B:
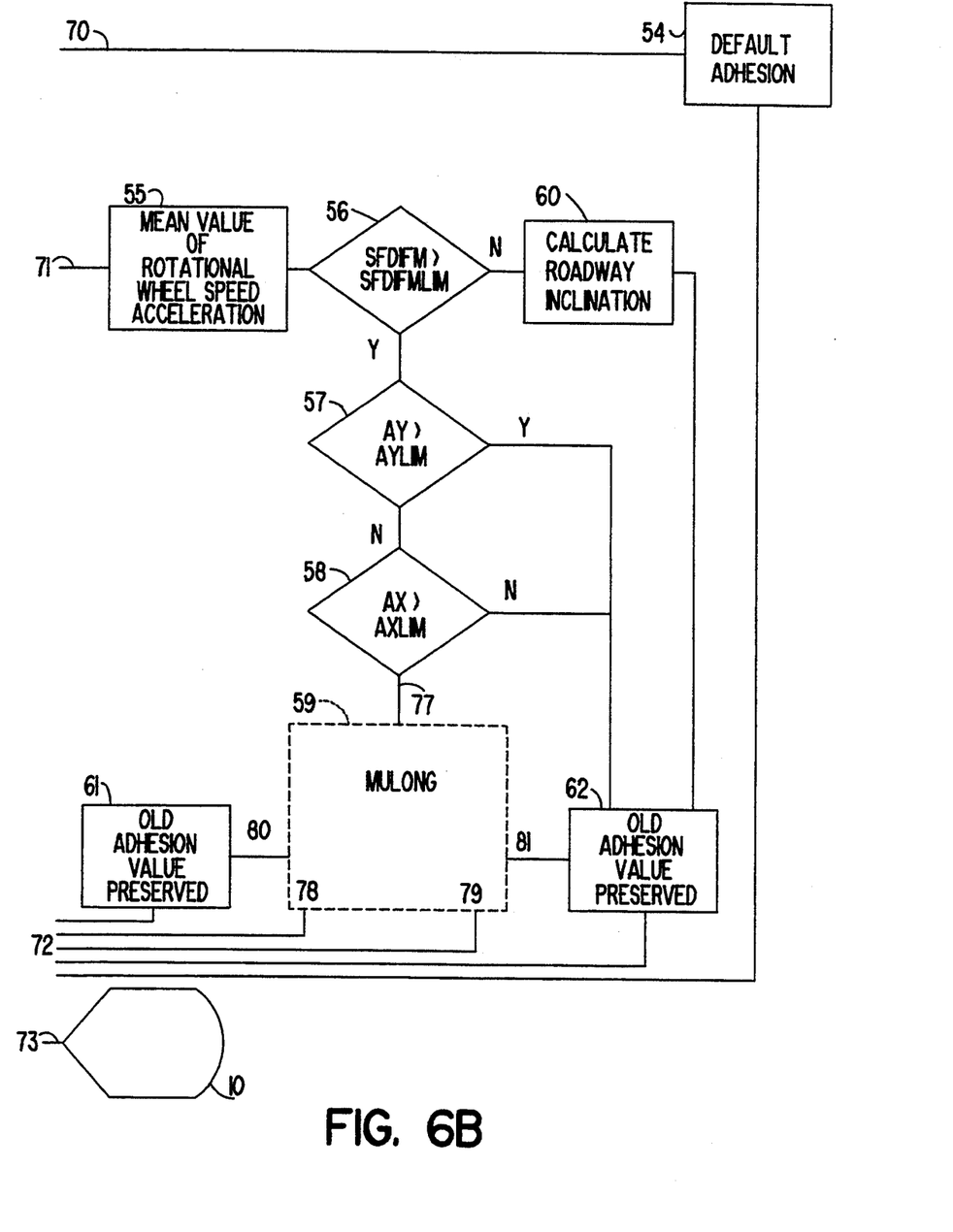

If the steering angle is greater than ASTLIM, the decision is made at 44 whether the transverse acceleration ay is greater than aylim, i.e., sufficiently great. If not, the decision is made at 51 whether the steering angle AST is greater than another limit value AST_R_LIM after which the vehicle could slide in a straight line, which is verified at 53, and leads directly to the end of the computing cycle at 50. If not, the old adhesion value is preserved.

If the decision is made at 44 that the transverse acceleration ay is greater than aylim, the decision is made whether the first derivative of the steering angle ASTDIF is greater than a limit value ASTDIFLIM (indicating steering wheel rotation) and if this is the case, the old adhesion value is preserved. If not, the longitudinal acceleration ax is compared with a limit value axlim. If the longitudinal acceleration value ax is too low, the decision is made at 47 to ascertain only the adhesion value in transverse direction. If the longitudinal acceleration ax is greater than axlim, the general adhesion value is determined in box 48 the contents of which can be seen in FIG. 6C. The corresponding connecting lines are lines 74, 75 and 76. The latter two lead once again to the determination of the safety margin at 50.

If the steering angle AST at 43 is smaller than ASTLIM, line 71 leads to the determination of the mean value of the wheel speed acceleration at 55 to 56 (FIG. 6B) where the decision is made whether this mean value SFDIFM is greater than a limit value SFDIFMLIM. If not, the inclination of the roadway must be calculated at 60 for the purpose of compensation and the old adhesion value is preserved at 62. If it is greater, the decision is made at 57 whether the transverse acceleration ay is greater than aylim, and the decision is made at 58 whether the longitudinal acceleration ax is greater than a limit value axlim.

If the transverse acceleration ay is greater and the longitudinal acceleration ax is not greater than their respective limit values, no new adhesion value in the longitudinal direction can be ascertained and the old adhesion value is preserved at 62. On the other hand, if the transverse acceleration ay is lower than the limit value aylim and the longitudinal acceleration ax is above the limit value axlim, the adhesion value in longitudinal direction can be determined at 59 (see FIG. 6D).

Figure 6C:
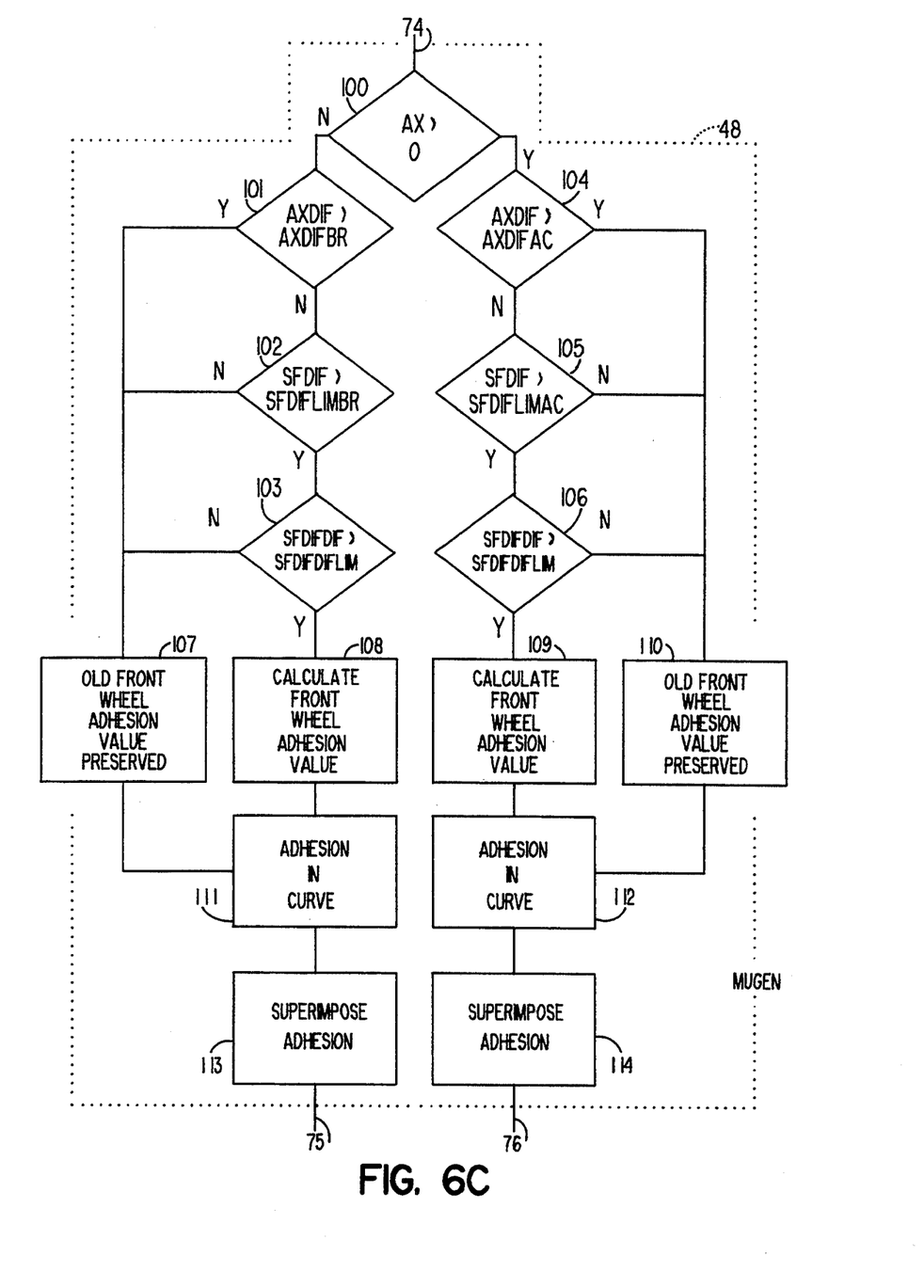

FIG. 6C shows the program execution in detail if a general adhesion value is calculated. At 100 the longitudinal acceleration ax is compared with zero between braking and acceleration. From 101 to 106 the decision is made whether the differentiations of the longitudinal acceleration ax and of the rotational wheel speed SF (note that SFDIF=Phi) are greater or smaller than predetermined values, and depending on the case, the old adhesion value is preserved at 107 and 100, or a new adhesion value is calculated at 108 and 109. At 113 and 114 the adhesion values for transverse direction of box 47 are superimposed on the newly ascertained adhesion values from 111, 112, to obtain general adhesion values and the values obtained in this manner are taken by lines 75, 76 to compute the safety margins at 50.

Figure 6D:
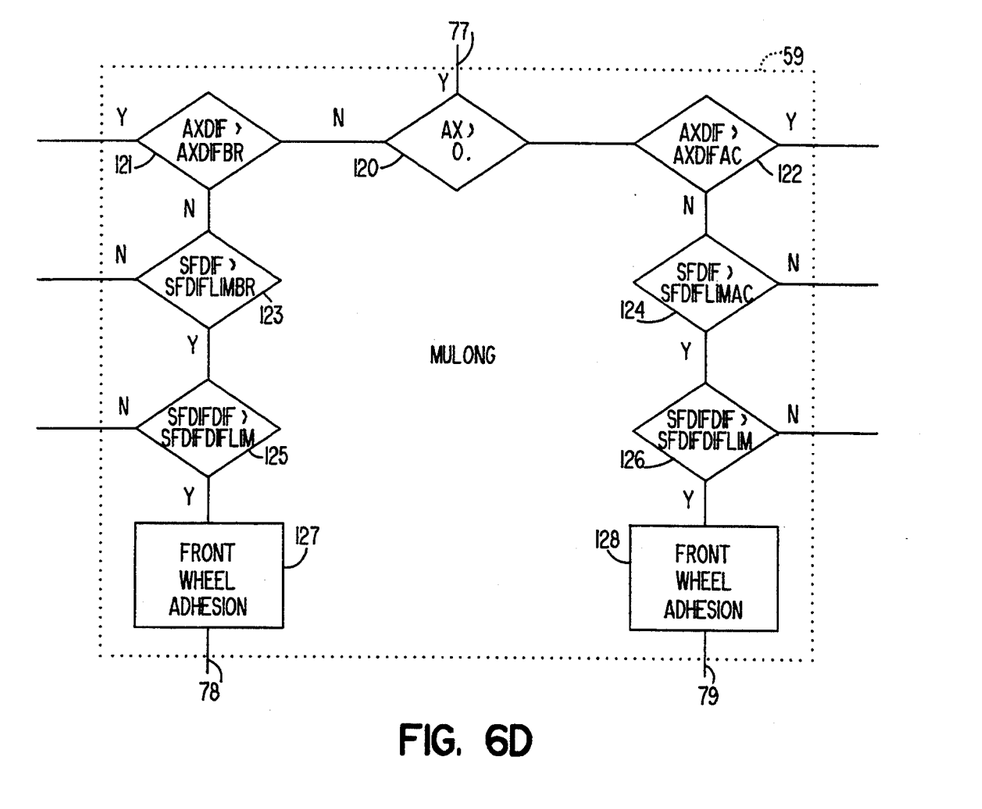

FIG. 6D shows the program execution in detail for the computation of the adhesion value in the longitudinal direction (Six) which occurs when the longitudinal acceleration ax has exceeded the minimum value axlim in box 58. It is then first decided at 120 whether the longitudinal acceleration ax is positive or negative, i.e., whether a braking or an accelerating event is involved. Now the longitudinal acceleration ax and the rotational wheel speed SF are compared in the appropriate differentiation steps with limit values, in a manner similar to FIG. 6C, and it is decided according to these criteria whether the old adhesion value should be preserved (lines 80 and 81 leading to boxes 61 and 62 in FIG. 6B), or whether the adhesion value in longitudinal direction should be computed anew (127 and 128). This decision is made at 121 to 126 and is represented by the hatched surfaces in FIG. 4. The ensuing commands lead along lines 78, 79 to the computation of the safety margin at 50. The latter follows the mathematical principles of the computation of SAFLIM as described earlier and is connected to the display 10.

Figure 7:
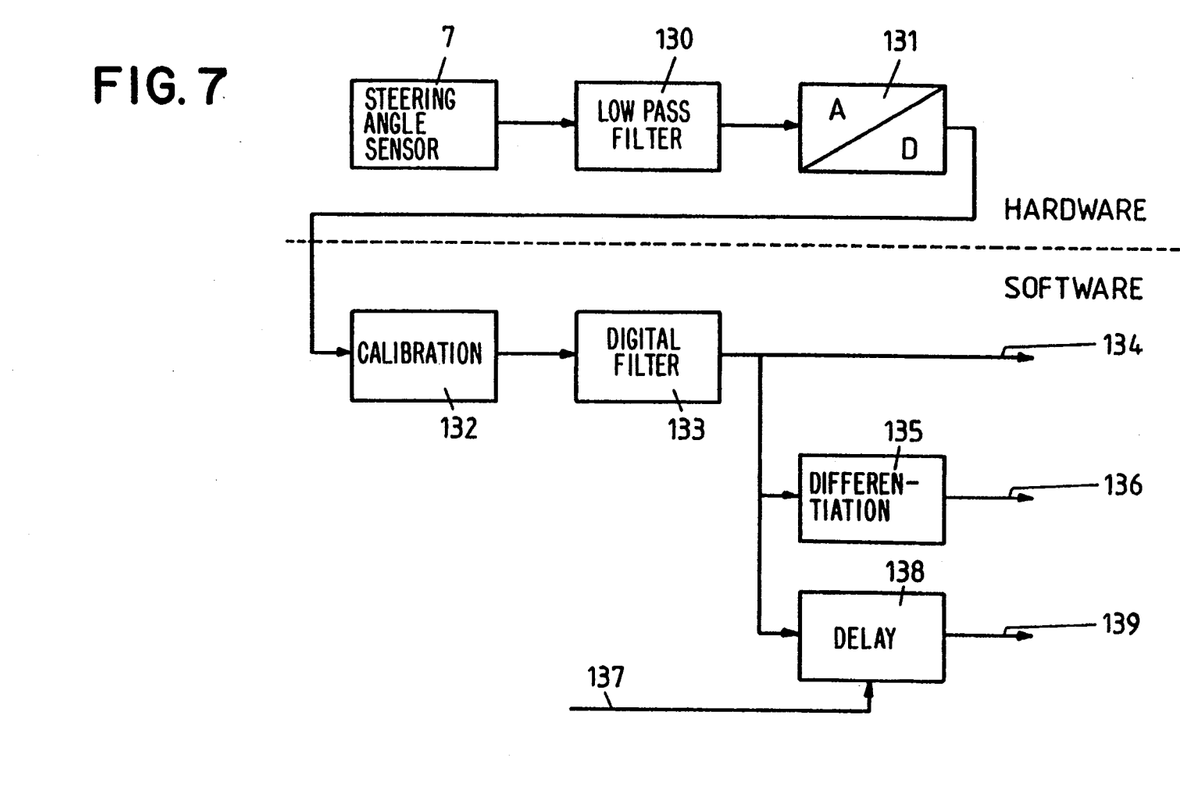
FIG. 7 is a schematic representation of the editing of the steering angle signal.

FIG. 7 shows an example of editing of the steering angle signal. The signal coming from the steering angle sensor 7 runs through a low pass filter 130, then through an analog/digital converter 131, a calibration station 132 and digital filters 133. At 134 the edited steering angle signal AST is then available. From this signal AST, a differentiated signal ASTDIF, is obtained in a differentiation station 135, and becomes available at 136. Furthermore, the edited steering angle signal AST is also transmitted to delay element 138 the delay time of which is set as a function of the longitudinal vehicle speed transmitted via line 137, and from which a delayed steering angle signal is available at 139. This makes it possible to take into account the sluggishness of reaction time of the tire running surface to movements of the steering wheel.

While the invention has been described by reference to specific embodiments, this was for purposes of illustration only. Numerous alternative embodiments will be apparent to those skilled in the art and are considered to be within the scope of the invention.

We claim:

1. A process for determining a safety margin with respect to adhesion between tires and roadway of a motor vehicle travelling along a direction of travel under all conditions of travel comprising detecting by means of at least one acceleration sensor located on said motor vehicle longitudinal and transverse acceleration values (ax, ay) for said motor vehicle along directions which are longitudinal and transverse to the direction of travel and producing signals indicative thereof, detecting by means of a rotational wheel sensor a rotational wheel acceleration (Phi) for said motor vehicle and producing a signal indicative thereof, detecting by means of a steering angle sensor a dynamic steering angle for said motor vehicle and producing a signal indicative thereof, receiving all of said signals in an electronic processor under all conditions of travel and by means of said electronic processor determining a transverse adhesion value (Siy) as a function of said transverse acceleration value (ay) and said dynamic steering angle, by means of said electronic processor determining a longitudinal adhesion value (Six) as a function of said longitudinal acceleration value (ax) and said rotational wheel acceleration (Phi), by means of said electronic processor determining a maximum attainable longitudinal acceleration value (axLIM) and a maximum attainable transverse acceleration value (ayLIM) by multiplying said longitudinal acceleration value (Six) and said transverse acceleration value (Siy) by vehicle specific coefficients (Kx, Ky) respectively, establishing a limit curve (aLIM) from the maximum attainable acceleration values (axLIM, ayLIM), forming a current vehicle movement state vector (AF) from a vectorial combination of the longitudinal acceleration (ax) and the transverse acceleration (ay) values, by means of said electronic processor determining a safety margin value (SAFLIM) under all conditions of travel by comparing the lengths of said vehicle movement state vector (AF) with a collinear limit vector (AMAX) which reaches said limit curve (aLIM), and on a display device displaying said safety margin value (SAFLIM) under all conditions of travel.

2. The process of claim 1 wherein said limit curve (aLIM) is stored in said electronic processor and updated when said vehicle movement state vector (AF) changes.

3. The process of claim 2 wherein said limit curve (aLIM) is corrected by affine transformation when said vehicle movement state vector (AF) changes.

4. The process of claim 1 wherein said longitudinal adhesion value (Six) is determined from an analytically represented function of said rotational wheel acceleration (Phi) and said longitudinal acceleration (ax), and wherein said transverse adhesion value (Siy) is determined from an analytically represented function of said transverse acceleration (ay) and said dynamic steering angle.

5. The process of claim 4 wherein said vehicle specific coefficients (Kx, Ky) are obtained from prior tests of said motor vehicle.

6. The process of claim 4 wherein said vehicle specific coefficients (Kx, Ky) are obtained from prior computer simulations of said motor vehicle.

7. The process of claim 1 wherein said safety margin value (SAFLIM) is compared with at least one predetermined threshold value, and wherein a perceptible warning signal is triggered when said threshold value is exceeded.

8. The process of claim 1 wherein current longitudinal and transverse adhesion values (Six, Siy) are used only when they are within predetermined limit values.

9. The process of claim 1 wherein said dynamic steering angle signal is received at said electronic processor after a time delay.

10. The process of claim 1 wherein said electronic procesosr introduces correction values in said longitudinal adhesion value (Six) and in said transverse adhesion value (Siy) when said roadway is inclined.

* * * * *